(12) United States Patent
Lipari et al.

(10) Patent No.: US 6,232,333 B1
(45) Date of Patent: *May 15, 2001

(54) PHARMACEUTICAL COMPOSITION

(75) Inventors: John Lipari, Racine, WI (US); Laman A. Al-Razzak, Lake Forest, IL (US); Soumojeet Ghosh, Lindenhurst, IL (US); Rong Gao, Park City, IL (US); Dilip Kaul, Gurnee, IL (US)

(73) Assignee: Abbott Laboratories, Abbott Park, IL (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/966,495

(22) Filed: Nov. 7, 1997

Related U.S. Application Data

(60) Provisional application No. 60/031,463, filed on Nov. 21, 1996, now abandoned.

(51) Int. Cl.$^7$ .................. A61K 31/425; A61K 31/42; A01N 43/78; A01N 43/76
(52) U.S. Cl. .................. 514/365; 514/374; 514/369; 514/370; 514/376; 514/377
(58) Field of Search .................. 514/365, 374, 514/369, 370, 376, 377

(56) References Cited

U.S. PATENT DOCUMENTS

| | | | |
|---|---|---|---|
| 4,997,851 | 3/1991 | Isaacs et al. | 514/558 |
| 5,196,438 | 3/1993 | Martin et al. | 514/311 |
| 5,413,999 | 5/1995 | Vacca et al. | 514/231.5 |
| 5,484,801 | 1/1996 | Al-Razzak et al. | 514/365 |
| 5,484,926 | 1/1996 | Dressman et al. | 546/114 |
| 5,541,206 | 7/1996 | Kempf et al. | 514/365 |
| 5,559,158 | 9/1996 | Al-Razzak et al. | 514/616 |
| 5,725,878 | 3/1998 | Al-Razzak et al. | 424/456 |
| 5,914,332 | 6/1999 | Sham et al. | 514/274 |
| 5,948,436 | 7/1999 | Al-Razzak et al. | 424/456 |

FOREIGN PATENT DOCUMENTS

| | | | |
|---|---|---|---|
| 0490667 | 6/1992 | (EP) | C07K/5/02 |
| 490667 | 6/1992 | (EP) | C07K/5/02 |
| 0580402 | 1/1993 | (EP) | C07C/271/20 |
| 0532466 | 3/1993 | (EP) | C07K/5/04 |
| 532466 | 3/1993 | (EP) | C07K/5/04 |
| 0541168 | 5/1993 | (EP) | C07D/217/26 |
| 0560268 | 9/1993 | (EP) | C07D/211/60 |
| 560268 | 9/1993 | (EP) | C07D/211/60 |
| 580402 | 1/1994 | (EP) | C07C/23/20 |
| 9208701 | 5/1992 | (WO) | C07D/215/48 |
| WO 92/08701 | 5/1992 | (WO) | C07N/215/48 |
| 9307128 | 10/1992 | (WO) | C07D/243/04 |
| WO 93/07128 | 4/1993 | (WO) | C07D/243/04 |
| 9323368 | 11/1993 | (WO) | C07D/275/24 |
| WO 93/23368 | 11/1993 | (WO) | C07C/275/24 |
| 9405639 | 3/1994 | (WO) | C07D/215/48 |
| WO 94/05639 | 3/1994 | (WO) | C07D/215/48 |
| 9506061 | 3/1995 | (WO) | C07K/5/03 |
| 9509614 | 4/1995 | (WO) | A61K/9/14 |
| 9509843 | 4/1995 | (WO) | C07D/217/26 |
| 9520384 | 8/1995 | (WO) | A61K/31/425 |
| 9530670 | 11/1995 | (WO) | C07D/309/32 |
| WO 95/30670 | 11/1995 | (WO) | C07D/309/32 |
| WO 96/03113 | 2/1996 | (WO) | A61K/9/107 |
| 9701349 | 1/1997 | (WO) | A61K/38/06 |
| 9720554 | 6/1997 | (WO) | A61K/31/34 |
| WO 97/21685 | 6/1997 | (WO) | C07D/239/10 |

OTHER PUBLICATIONS

Mimoto, et al., Chem Pharm Bull. 40 (8) 2251–2253 (1992).
Kempf, et al., Proc. Natl. Acad Sci. USA 92 2484 (1995).
Mazur, et al., Chem Abstr. 83: 1409r (1975).

*Primary Examiner*—Russell Travers
(74) *Attorney, Agent, or Firm*—Steven R. Crowley

(57) ABSTRACT

A liquid pharmaceutical composition providing improved oral bioavailability is disclosed for compounds which are inhibitors of HIV protease. In particular, the composition comprises a solution in a pharmaceutically acceptable organic solvent of (a) the HIV protease inhibitor and, optionally, (b) a surfactant. The composition can optionally be encapsulated in either hard gelatin capsules or soft elastic capsules (SEC).

16 Claims, No Drawings

PHARMACEUTICAL COMPOSITION

This application claims the benefit of U.S. Provisional Application for Patent No. 60/031,463, filed Nov. 21, 1996 now abandoned.

TECHNICAL FIELD

A liquid pharmaceutical composition providing improved oral bioavailability is disclosed for compounds which are inhibitors of HIV protease. In particular, the composition is a solution which comprises (a) the HIV protease inhibitor, (b) a pharmaceutically acceptable organic solvent and, optionally, (c) a surfactant. The composition can optionally be encapsulated in either hard gelatin capsules or soft elastic capsules (SEC).

BACKGROUND OF THE INVENTION

One measure of the potential usefulness of an oral dosage form of a new pharmaceutical agent is the bioavailability observed after oral administration of the dosage form. Various factors can affect the bioavailability of a drug when administered orally. These factors include aqueous solubility, drug absorption throughout the gastrointestinal tract, dosage strength and first: pass effect. Aqueous solubility is one of the most important of these factors. When a drug has poor aqueous solubility, attempts are often made to identify salts or other derivatives of the drug which have improved aqueous solubility. When a salt or other derivative of the drug is identified which has good aqueous solubility, it is generally accepted that an aqueous solution formulation of this salt or derivative will provide the optimum oral bioavailability. The bioavailability of the oral solution formulation of a drug is then generally used as the standard or ideal bioavailability against which other oral dosage forms are measured.

For a variety of reasons, such as patient compliance and taste masking, a solid dosage form, such as capsules, is usually preferred over a liquid dosage form. However, oral solid dosage forms of a drug generally provide a lower bioavailability than oral solutions of the drug. One goal of the development of a suitable capsule dosage form is to obtain a bioavailability of the drug that is as close as possible to the ideal bioavailability demonstrated by the oral solution formulation of the drug.

It has recently been determined that HIV protease inhibiting compounds are useful for inhibiting HIV protease in vitro and in vivo, are useful for inhibiting HIV (human immunodeficiency virus) infections and are useful for treating AIDS (acquired immunodeficiency syndrome). HIV protease inhibiting compounds typically are characterized by having poor oral bioavailability and there is a continuing need for the development of improved oral dosage forms for HIV protease inhibitors which have suitable oral bioavailability, stability and side effects profiles.

Examples of HIV protease inhibiting compounds include N-(2(R)-hydroxy-1(S)-indanyl)-2(R)-phenylmethyl-4(S)-hydroxy-5-(1-(4-(3-pyridylmethyl)-2(S)-N'-(t-butylcarboxamido)-piperazinyl))-peritaneamide (i.e., indinavir) and related compounds, disclosed in European Patent Application No. EP541168, published May 12, 1993, and U.S. Pat. No. 5,413,999, issued May 9, 1995 which are both incorporated herein by reference; N-tert-butyl-decahydro-2-[2(R)-hydroxy-4-phenyl-3(S)-[[N-(2-quinolylcarbonyl)-L-asparaginyl]amino]butyl]-(4aS,8aS)-isoquinoline-3(S)-carboxamide (i.e., saquinavir) and related compounds, disclosed in U.S. Pat. No. 5,196,438, issued Mar. 23, 1993, which is incorporated herein by reference; 5(S)-Boc-amino-4(S)-hydroxy-6-phenyl-2(R)-phenylmethylhexanoyl-(L)-Val-(L)-Phe-morpholin-4-ylamide and related compounds, disclosed in European Patent Application No. EP532466, published Mar. 17, 1993, which is incorporated herein by reference;

1-Naphthoxyacetyl-beta-methylthio-Ala-(2S,3S)-3-amino-2-hydroxy-4-butanoyl-1,3-thiazolidine-4-t-butylamide (i.e., 1-Naphthoxyacetyl-Mta-(2S,3S)-AHPBA-Thz-NH-tBu), 5-isoquinolinoxyacetyl-beta-methylthio-Ala-(2S,3S)-3-amino-2-hydroxy-4-butanoyl-1,3-thiazolidine-4-t-butylamide (i.e., iQoa-Mta-Apns-Thz-NHtBu) and related compounds, disclosed in European Patent Application No. EP490667, published Jun. 17, 1992 and Chem. Pharm. Bull. 40 (8) 2251 (1992), which are both incorporated herein by reference;

[1S-[1R*(R*),2S*]]-N$^1$[3-[[[(1,1-dimethylethyl)amino]carbonyl](2-methylpropyl)amino]-2-hydroxy-1-(phenylmethyl)propyl]-2-[(2-quinolinylcarbonyl)amino]-butanediamide (i.e., SC-52151) and related compounds, disclosed in PCT Patent Application No. WO92/08701, published May 29, 1992 and PCT Patent Application No. WO93/2336, published Nov. 25, 1993, both of which are incorporated herein by reference;

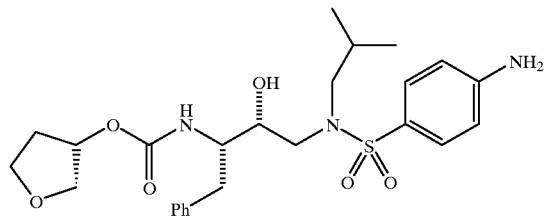

(i.e., VX-478) and related compounds, disclosed in PCT Patent Application No. WO94/05639, published Mar. 17, 1994, which is incorporated herein by reference;

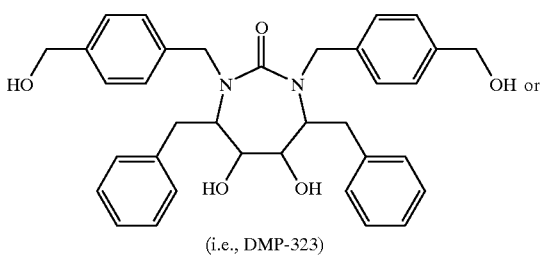

(i.e., DMP-323)

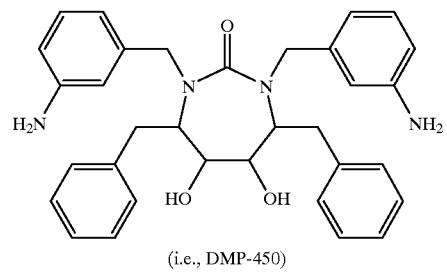

(i.e., DMP-450)

and related compounds, disclosed in PCT Patent Application No. WO93/07128, published Apr. 15, 1993, which is incorporated herein by reference;

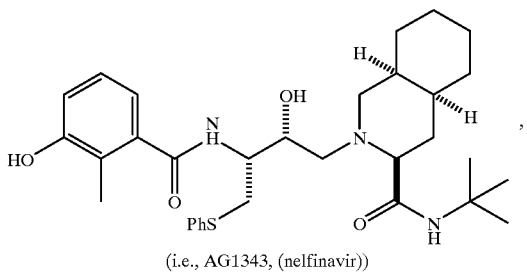

(i.e., AG1343, (nelfinavir))

disclosed in PCT Patent Application No. WO95/09843, published Apr. 13, 1995 and U.S. Pat. No. 5,484,926, issued Jan. 16, 1996, which are both incorporated herein by reference;

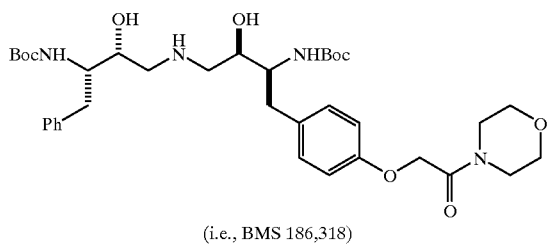

(i.e., BMS 186,318)

disclosed in European Patent Application No. EP580402, published Jan. 26, 1994, which is incorporated herein by reference;

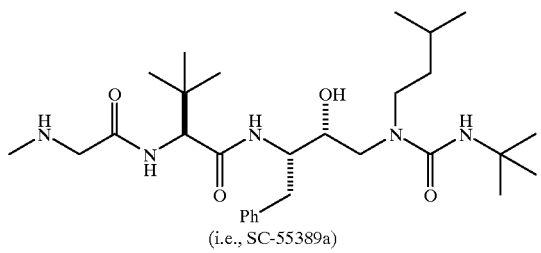

(i.e., SC-55389a)

and related compounds disclosed in PCT Patent Application No. WO 9506061, published Mar. 2, 1995, which is incorporated herein by reference and at 2nd National Conference on Human Retroviruses and Related Infections, (Washington, D.C., Jan. 29–Feb. 2, 1995), Session 88; and

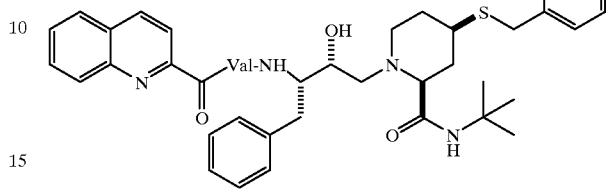

(i.e., BILA 1096 BS) and related compounds disclosed in European Patent Application No. EP560268, published Sep. 15, 1993, which is incorporated herein by reference; and

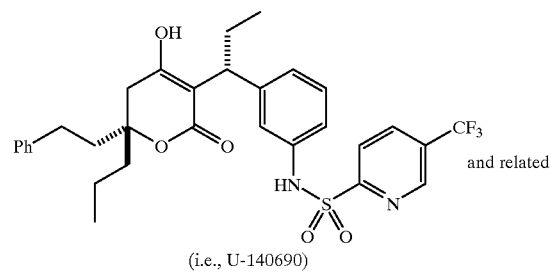

(i.e., U-140690)

and related compounds disclosed in PCT Patent Application No. WO 9530670, published Nov. 16, 1995, which is incorporated herein by reference; or a pharmaceutically acceptable salt of any of the above.

Other examples of HIV protease inhibiting compounds include compounds of the formula I:

I

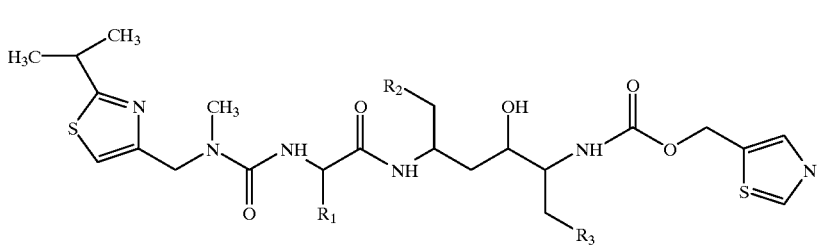

wherein $R_1$ is lower alkyl and $R_2$ and $R_3$ are phenyl and related compounds or a pharmaceutically acceptable salt thereof, disclosed in PCT Patent Application No. WO94114436, published Jul. 7, 1994 and U.S. Pat. No. 5,541,206, issued Jul. 30, 1996, both of which are incorporated herein by reference. The compounds of formula I are useful to inhibit HIV infections and, thus, are useful for the treatment of AIDS.

In particular, the compound of formula II, has been found to be especially effective as an inhibitor of HIV protease.

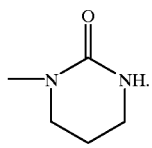

A most preferred compound of the formula IV is (2S,3S, 5S)-2-(2,6-Dimethylphenoxyacetyl)amino-3-hydroxy-5-

II

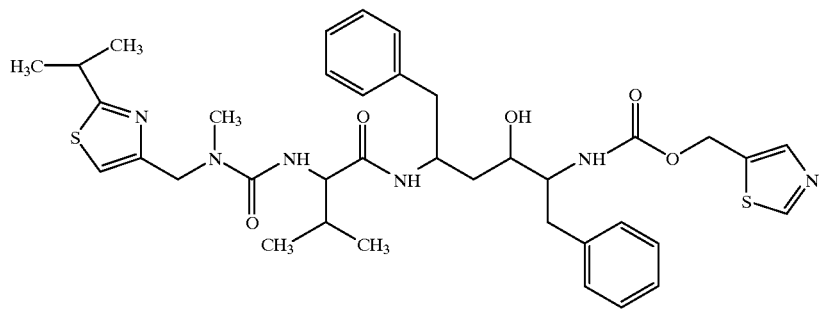

The most preferred compound of formula II is (2S,3S,:5S)-5-(N-(N-((N-Methyl-N-((2-isopropyl-4-thiazolyl)methyl)-amino)carbonyl)valinyl)amino)-2-(N-((5-thiazolyl)methoxycarbonyl)amino)-1,6-diphenyl-3-hydroxyhexane (ritonavir; compound III) or a pharmaceutically acceptable salt thereof.

Other examples of HIV protease inhibiting compounds also include compounds of the formula IV:

IV

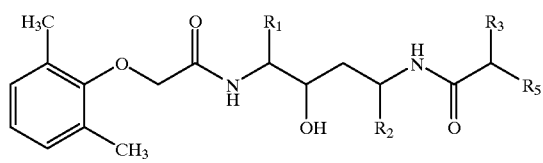

wherein $R_1$ is benzyl, $R_2$ is benzyl or loweralkyl, $R_3$ is loweralkyl and $R_5$ is

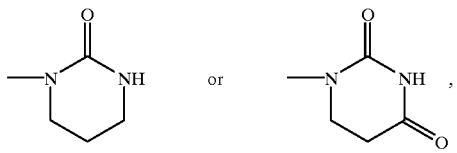

and related compounds or a pharmaceutically acceptable salt thereof, disclosed in U.S. patent application Ser. No. 08/572,226, filed Dec. 13, 1996 and U.S. patent application Ser. No. 08/753,201, filed Nov. 21, 1996 and International Patent Application No. WO97/21685, published Jun. 19, 1997, all of which are incorporated herein by reference.

A preferred compound is the compound of formula IV wherein $R_1$ and $R_2$ are benzyl, $R_3$ is isopropyl and $R_5$ is [2S-(1-tetrahydro-pyrimid-2-onyl)-3-methyl butanoyl] amino-1,6-diphenylhexane (compound V) or a pharmaceutically acceptable salt thereof. The preparation of compound V is disclosed in U.S. patent application Ser. No. 08/572,226, filed Dec. 13,1996 and U.S. patent application Ser. No. 08/753,201, filed Nov. 21, 1996 and International Patent Application No. WO97/21685, published Jun. 19, 1997.

Compound III has an aqueous solubility of approximately 6 micrograms per milliliter at pH>2. This is considered to be extremely poor aqueous solubility and, therefore, compound III in the free base form would be expected to provide very low oral bioavailability. In fact, the free base form of compound III, administered as an unformulated solid in a capsule dosage form, is characterized by a bioavailability of less than 2% following a 5 mg/kg oral dose in dogs.

Acid addition salts of compound III (for example, bis-hydrochloride, bis-tosylate, bis-methane sulfonate and the like) have aqueous solubilities of <0.1 milligrams/milliliter. This is only a slight improvement over the solubility of the free base. This low aqueous solubility would not make practical the administration of therapeutic amounts of an acid addition salt of compound III as an aqueous solution. Furthermore, in view of this low aqueous solubility, it is not surprising that the bis-tosylate of compound III, administered as an unformulated solid in a capsule dosage form, is characterized by a bioavailability of less than 2% following a 5 mg/kg oral dose in dogs.

In order to have a suitable oral dosage form of compound III, the oral bioavailability of compound III should be at least 20%. Preferably, the oral bioavailability of compound III from the dosage form should be greater than about 40% and, more preferably, greater than about 50%.

While some drugs would be expected to have good solubility in organic solvents, it would not necessarily follow that oral administration of such a solution would give good bioavailability for the drug. It has been found that compound III has good solubility in pharmaceutically acceptable organic solvents and that the solubility in such solvents is enhanced in the presence of a pharmaceutically acceptable long chain fatty acid. Administration of the solution as an encapsulated dosage form (soft elastic capsules or hard gelatin capsules) provides an oral bioavailability of as high as about 60% or more.

DISCLOSURE OF THE INVENTION

In accordance with the present invention, there is a pharmaceutical composition which is a solution comprising
(a) an HIV protease inhibiting compound or a combination of HIV protease inhibiting compounds (preferably, a compound of the formula II or IV or saquinavir or nelfinavir or indinavir or VX-478, more preferably, a compound of the formula III or V or saquinavir or nelfinavir or indinavir or VX-478, or a combination of a compound of the formula II or nelfinavir and another HIV protease inhibitor (preferably, the compound of the formula IV or saquinavir or indinavir or nelfinavir or VX-478), or, more preferably, a combination of a compound of the formula III or nelfinavir and another HIV protease inhibitor (preferably, the compound of the formula V or saquinavir or indinavir or nelfinavir or VX-478)),
(b) a pharmaceutically acceptable organic solvent which comprises a pharmaceutically acceptable long chain fatty acid or a mixture of a pharmaceutically acceptable long chain fatty acid and a pharmaceutically acceptable alcohol, and, optionally,
(c) a pharmaceutically acceptable surfactant.

In the above solution composition, preferred HIV protease inhibitors as individual compounds are the compound of the formula III or V or saquinavir or nelfinavir or indinavir or VX-478. In the above composition, preferred combinations of HIV protease inhibitors are the compound of formula III and the compound of formula V, the compound of formula III and saquinavir, the compound of formula III and indinavir, the compound of formula III and nelfinavir, the compound of formula III and VX-478, nelfinavir and the compound of formula V, nelfinavir and saquinavir, nelfinavir and indinavir, nelfinavir and VX-478.

Also in accordance with the present invention, there is a pharmaceutical composition which is a solution comprising
(a) an HIV protease inhibiting compound or a combination of HIV protease inhibiting compounds (preferably, a compound of the formula II or IV or saquinavir or nelfinavir or indinavir or VX-478, more preferably, a compound of the formula III or V or saquinavir or nelfinavir or indinavir or VX-478, or a combination of a compound of the formula II or nelfinavir and another HIV protease inhibitor (preferably, the compound of the formula IV or saquinavir or indinavir or nelfinavir or VX-478), or, more preferably, a combination of a compound of the formula III or nelfinavir and another HIV protease inhibitor (preferably, the compound of the formula V or saquinavir or indinavir or nelfinavir or VX-478)),
(b) a pharmaceutically acceptable organic solvent which comprises a pharmaceutically acceptable long chain fatty acid or a mixture of a pharmaceutically acceptable long chain fatty acid and a pharmaceutically acceptable alcohol, and, optionally,
(c) a pharmaceutically acceptable surfactant, wherein the solution is encapsulated in a soft elastic gelatin capsule (SEC) or a hard gelatin capsule.

In the above enacpsulated solution composition, preferred HIV protease inhibitors as individual compounds are the compound of the formula III or V or saquinavir or nelfinavir or indinavir or VX-478. In the above composition, preferred combinations of HIV protease inhibitors are the compound of formula III and the compound of formula V, the compound of formula III and saquinavir, the compound of formula III and indinavir, the compound of formula III and nelfinavir, the compound of formula III and VX-478, nelfinavir and the compound of formula V, nelfinavir and saquinavir, nelfinavir and indinavir, nelfinavir and VX-478.

The solution composition of the invention can also comprise an antioxidant (for example, ascorbic acid, BHA (butylated hydroxyanisole), BHT (butylated hydroxytoluene), vitamin E, vitamin E PEG 1000 succinate and the like) for chemical stability.

The compositions of this invention (solution or encapsulated solution) provide improved oral bioavailability for HIV protease inhibitors. In particular, the compositions of this invention (solution or encapsulated solution) provide improved oral bioavailability for compound III when compared to non-formulated compound III (base) or non-formulated compound III (acid addition salt).

The term "pharmaceutically acceptable long chain fatty acid" as used herein refers to saturated, mono-unsaturated or di-unsaturated $C_{12}$ to $C_{18}$ carboxylic acids which are liquids at room temperature. Preferred long chain fatty acids are mono-unsaturated $C_{16}$–$C_{20}$ carboxylic acids which are liquids at room temperature. A most preferred long chain fatty acid is oleic acid.

The term "pharmaceutically acceptable alcohol" as used herein refers to alcohols which are liquids at about room temperature, approximately 20° C., for example, ethanol, propylene glycol, 2-(2-ethoxyethoxy)ethanol (Transcutol®, Gattefosse, Westwood, N.J. 07675), benzyl alcohol, glycerol, polyethylene glycol 200, polyethylene glycol 300, polyethylene glycol 400 and the like. A preferred pharmaceutically acceptable alcohol is ethanol or propylene glycol or a mixture thereof.

The term "pharmaceutically acceptable surfactant" as used herein refers to a pharmaceutically acceptable non-ionic surfactant for example, polyoxyethylene castor oil derivatives (for example, polyoxyethyleneglyceroltriricinoleate or polyoxyl 35 castor oil (Cremophor®EL, BASF Corp.) or polyoxyethyleneglycerol oxystearate (Cremophor®RH 40 (polyethyleneglycol 40 hydrogenated castor oil)) or Cremophor®RH 60 (polyethyleneglycol 60 hydrogenated castor oil), BASF Corp. and the like) or block copolymers of ethylene oxide and propylene oxide, also known as polyoxyethylene polyoxypropylene block copolymers or polyoxyethylenepolypropylene glycol, such as Poloxamer®124, Poloxamer®188, Poloxamer®237, Poloxamer®388, Poloxamer®407 and the like, (BASF Wyandotte Corp.) or a mono fatty acid ester of polyoxyethylene (20) sorbitan (for example, polyoxyethylene (20) sorbitan monooleate (Tween® 80), polyoxyethylene (20) sorbitan monostearate (Tween® 60), polyoxyethylene (20) sorbitan monopalmitate (Tween® 40), polyoxyethylene (20) sorbitan monolaurate (Tween® 20) and the like) and the like) or a sorbitan fatty acid ester (including sorbitan laurate, sorbitan oleate, sorbitan palmitate, sorbitan stearate and the like). A preferred pharmaceutically acceptable surfactant is polyoxyl 35 castor oil (Cremophor®EL, BASF Corp.), polyoxyethylene (20) sorbitan monolaurate (Tween® 20), polyoxyethylene (20) sorbitan monooleate (Tween® 80) or a sorbitan fatty acid ester, for example sorbitan oleate. A most preferred pharmaceutically acceptable surfactant is polyoxyl 35 castor oil (Cremophor®EL, BASF Corp.).

A preferred composition of the invention is a solution comprising
(a) an HIV protease inhibiting compound or a combination of HIV protease inhibiting compounds (preferably, a compound of the formula II or IV or saquinavir or nelfinavir or indinavir or, more preferably, a compound of the formula III or V or saquinavir or nelfinavir or indinavir, or, most preferably, a compound of the formula III or V); or a combination of a compound of the formula II or nelfinavir and another HIV protease inhibitor (preferably, the compound of the formula IV or saquinavir or indinavir or nelfinavir, or, more preferably, a combination of a compound of the formula III or nelfinavir and another HIV protease inhibitor (preferably, the compound of the formula V or saquinavir or indinavir or nelfinavir), or, most preferably, a combination of a compound of formula III and a compound of formula V) in the amount of from about 1% to about 50% (preferably, from about 1% to about 40%; more preferably, from about 10% to about 40%; most preferably, from about 15% to about 40%) by weight of the total solution, (b) a pharmaceutically acceptable organic solvent which comprises (i) a pharmaceutically acceptable long chain fatty acid in the amount of from about 20% to about 99% (preferably, from about 30% to about 70%; more preferably, from about 40% to about 60%) by weight of the total solution or (ii) a mixture of (1) a pharmaceutically acceptable long chain fatty acid in the amount of from about 20% to about 99% (preferably, from about 30% to about 70%; more preferably, from about 40% to about 60%) by weight of the total solution and (2) a pharmaceutically acceptable alcohol in the amount of from about 0% to about 15% (preferably, from about 6% to about 12%) by weight of the total solution and (c) a pharmaceutically acceptable surfactant in the amount of from about 0% to about 40% (preferably, from about 2% to about 20% and most preferably, from about 5% to about 15%) by weight of the total solution. In a preferred embodiment of the invention, the solution is encapsulated in a soft elastic gelatin capsule (SEC) or a hard gelatin capsule.

Preferably, the pharmaceutically acceptable organic solvent comprises from about 50% to about 99% by weight of the total solution. More preferably, the pharmaceutically acceptable organic solvent or mixture of pharmaceutically acceptable organic solvents comprises from about 50% to about 75% by weight of the total solution.

Preferred pharmaceutically acceptable solvents comprise (1) a pharmaceutically acceptable long chain fatty acid in the amount of from about 40% to about 70% by weight of the total solution and (2) ethanol or propylene glycol in the amount of from about 1% to about 15% by weight of the total solution or a mixture of ethanol and propylene glycol in the amount of from about 1% to about 15% by weight of the total solution. More preferred pharmaceutically acceptable solvents comprise (1) a pharmaceutically acceptable long chain fatty acid in the amount of from about 40% to about 70% by weight of the total solution and (2) ethanol in the amount of from about 10% to about 12% by weight of the total solution or propylene glycol in the amount of from about 5% to about 10% by weight of the total solution or a mixture of ethanol and propylene glycol in the amount of from about 5% to about 15% by weight of the total solution. Even more preferred pharmaceutically acceptable solvents comprise (1) oleic acid in the amount of from about 40% to about 70% by weight of the total solution and (2) ethanol in the amount of from about 10% to about 12% by weight of the total solution or propylene glycol in the amount of from about 5% to about 10% by weight of the total solution or a mixture of ethanol and propylene glycol in the amount of from about 10% to about 15% by weight of the total solution.

In one embodiment of the invention, a more preferred composition of the invention is a solution comprising (a) ritonavir in the amount of from about 1% to about 30% (preferably, from about 5% to about 25%) by weight of the total solution, (b) a pharmaceutically acceptable organic solvent which comprises (i) a pharmaceutically acceptable long chain fatty acid in the amount of from about 40% to about 99% (preferably, from about 30% to about 70%; more preferably, from about 40% to about 60%) by weight of the total solution or (ii) a mixture of (1) a pharmaceutically acceptable long chain fatty acid in the amount of from about 40% to about 99% (preferably, from about 030% to about 70%; more preferably, from about 40% to about 60%) by weight of the total solution and (2) a pharmaceutically acceptable alcohol in the amount of from about 0% to about 15% (preferably, from about 6% to about 12%) by weight of the total solution and (c) a pharmaceutically acceptable surfactant in the amount of from about 0% to about 20% (preferably, from about 5% to about 10%) by weight of the total solution. In a more preferred embodiment of the invention, the solution is encapsulated in a soft elastic gelatin capsule (SEC) or a hard gelatin capsule.

An even more preferred composition of the invention is a solution comprising (a) ritonavir in the amount of from about 1% to about 30% (preferably, from about 5% to about 25%) by weight of the total solution, (b) a pharmaceutically acceptable organic solvent which comprises (i) oleic acid in the amount of from about 15% to about 99% (preferably, from about 30% to about 70%; more preferably, from about 40% to about 60%) by weight of the total solution or (ii) a mixture of (1) oleic acid in the amount of from about 15% to about 99% (preferably, from about 30% to about 70%; more preferably, from about 40% to about 60%) by weight of the total solution and (2) ethanol in the amount of from about 0% to about 12% (preferably, from about 10% to about 12%) by weight of the total solution or propylene glycol in the amount of from about 0% to about 10% (preferably, from about 5% to about 10%) by weight of the total solution or a mixture thereof in the amount of from about 0% to about 15% (preferably, from about 10% to about 15%) by weight of the total solution and (c) polyoxyl 35 castor oil in the amount of from about 0% to about 20% (preferably, from about 5% to about 10%) by weight of the total solution. In an even more preferred embodiment of the invention, the solution is encapsulated in a soft elastic gelatin capsule (SEC) or a hard gelatin capsule.

A most preferred composition of the invention is a solution comprising (a) ritonavir in the amount of about 20% by weight of the total solution, (b) a pharmaceutically acceptable organic solvent which comprises a mixture of (1) oleic acid in the amount of from about 62% to about 64% by weight of the total solution and (2) ethanol in the amount of from about 10% to about 12%, preferably, about 12%, by weight of the total solution and (c) polyoxyl 35 castor oil in the amount of about 6% by weight of the total solution. In a most preferred embodiment of the invention, the solution is encapsulated in a soft elastic gelatin capsule (SEC) or a hard gelatin capsule and the solution also comprises an antioxidant (preferably, BHT (butylated hydroxytoluene)) in the amount of about 0.05% by weight of the total solution.

Another most preferred composition of the invention is a solution comprising
(a) ritonavir in the amount of about 20% by weight of the total solution,
(b) a pharmaceutically acceptable organic solvent which comprises a mixture of (1) oleic acid in the amount of about 65% by weight of the total solution and (2) ethanol in the amount of about 10% by weight of the total solution and
(c) polyoxyl 35 castor oil in the amount of about 5% by weight of the total solution. In a most preferred embodiment of the invention, the solution is encapsulated in a soft elastic gelatin capsule (SEC) or a hard gelatin capsule and the solution also comprises an antioxidant (preferably, BHT (butylated hydroxytoluene)) in the amount of from about 0.01% to about 0.08% by weight of the total solution (preferably, from about 0.01% to about 0.05% by weight of the total solution).

Another most preferred composition of the invention is a solution comprising
(a) ritonavir in the amount of about 20% by weight of the total solution,
(b) a pharmaceutically acceptable organic solvent which comprises a mixture of (1) oleic acid in the amount of about 60% by weight of the total solution and (2) ethanol in the amount of about 10% by weight of the total solution and
(c) polyoxyl 35 castor oil in the amount of about 10% by weight of the total solution. In a most preferred embodiment of the invention, the solution is encapsulated in a soft elastic gelatin capsule (SEC) or a hard gelatin capsule and the solution also comprises an antioxidant (preferably, BHT (butylated hydroxytoluene)) in the amount of from about 0.01% to about 0.08% by weight of the total solution (preferably, from about 0.01% to about 0.05% by weight of the total solution).

Another most preferred composition of the invention is a solution comprising
(a) ritonavir in the amount of about 20% by weight of the total solution,
(b) a pharmaceutically acceptable organic solvent which comprises a mixture of (1) oleic acid in the amount of about 70% by weight of the total solution and (2) a mixture of ethanol in the amount of about 5% by weight of the total solution and propylene glycol in the amount of about 5% by weight of the total solution. In a most preferred embodiment of the invention, the solution is encapsulated in a soft elastic gelatin capsule (SEC) or a hard gelatin capsule and the solution also comprises an antioxidant (preferably, BHT (butylated hydroxytoluene)) in the amount of from about 0.01% to about 0.08% by weight of the total solution (preferably, from about 0.01% to about 0.05% by weight of the total solution).

In another embodiment of the invention, a more preferred composition of the invention is a solution comprising
(a) (2S,3S,5S)-2-(2,6-dimethylphenoxyacetyl)amino-3-hydroxy-5-[2S-(1-tetrahydro-pyrimid-2-onyl)-3-methyl butanoyl]amino-1,6-diphenylhexane in the amount of from about 1% to about 50% (preferably, from about 5% to about 35%) by weight of the total solution,
(b) a pharmaceutically acceptable organic solvent which comprises (i) a pharmaceutically acceptable long chain fatty acid in the amount of from about 20% to about 99% (preferably, from about 30% to about 70%; more preferably, from about 40% to about 65%) by weight of the total solution or (ii) a mixture of (1) a pharmaceutically acceptable long chain fatty acid in the amount of from about 20% to about 99% (preferably, from about 30% to about 70%; more preferably, from about 40% to about 65%) by weight of the total solution and (2) a pharmaceutically acceptable alcohol in the amount of from about 0% to about 15% (preferably, from about 6% to about 12%) by weight of the total solution and
(c) a pharmaceutically acceptable surfactant in the amount of from about 0% to about 40% (preferably, from about 2% to about 20% and preferably, from about 5% to about 15%) by weight of the total solution. In a more preferred embodiment of the invention, the solution is encapsulated in a soft elastic gelatin capsule (SEC) or a hard gelatin capsule.

A more preferred composition of the invention is a solution comprising
(a) (2S,3S,5S)-2-(2,6-dimethylphenoxyacetyl)amino-3-hydroxy-5-[2S-(1-tetrahydro-pyrimid-2-onyl)-3-methyl butanoyl]amino-1,6-diphenylhexane in the amount of from about 1% to about 50% (preferably, from about 5% to about 35%) by weight of the total solution,
(b) a pharmaceutically acceptable organic solvent which comprises (i) oleic acid in the amount of from about 20% to about 99% (preferably, from about 30% to about 70%; more preferably, from about 40% to about 65%) by weight of the total solution or (ii) a mixture of (1) oleic acid in the amount of from about 20% to about 99% (preferably, from about 30% to about 70%; more preferably, from about 40% to about 65%) by weight of the total solution and (2) ethanol in the amount of from about 0% to about 12% (preferably, from about 10% to about 12%) by weight of the total solution or propylene glycol in the amount of from about 0% to about 10% (preferably, from about 5% to about 10%) by weight of the total solution or a mixture thereof in the amount of from about 0% to about 15% (preferably from about 5% to about 15%, most preferably, about 10%) by weight of the total solution and
(c) polyoxyl 35 castor oil in the amount of from about 0% to about 20% (preferably, from about 5% to about 10%) by weight of the total solution. In an even more preferred embodiment of the invention, the solution is encapsulated in a soft elastic gelatin capsule (SEC) or a hard gelatin capsule.

A most preferred composition of the invention is a solution comprising
(a) (2S,3S,5S)-2-(2,6-dimethylphenoxyacetyl)amino-3-hydroxy-5-[2S-(1-tetrahydro-pyrimid-2-onyl)-3-methyl butanoyl]amino-1,6-diphenylhexane in the amount of about 30% by weight of the total solution,
(b) a pharmaceutically acceptable organic solvent which comprises a mixture of (1) oleic acid in the amount of about 50% by weight of the total solution and (2) ethanol in the amount of about 10% by weight of the total solution and
(c) polyoxyl 35 castor oil in the amount of about 10% by weight of the total solution. In a most preferred embodiment of the invention, the solution is encapsulated in a soft elastic gelatin capsule (SEC) or a hard gelatin capsule and the solution also comprises an antioxidant (preferably, BHT (butylated hydroxytoluene)) in the amount of from about 0.01% to about 0.08% by weight of the total solution (preferably, from about 0.01% to about 0.05% by weight of the total solution).

In yet another embodiment of the invention, a more preferred composition of the invention is a solution comprising (a) a mixture of ritonavir in the amount of from about 1% to about 30% (preferably, from about 5% to about 25%) by weight of the total solution and another HIV protease inhibitor in the amount of from about 1% to about 50% (preferably, from about 5% to about 40%) by weight of the total solution, (b) a pharmaceutically acceptable organic solvent which comprises (i) a pharmaceutically acceptable long chain fatty acid in the amount of from about 10% to about 98% (preferably, from about 30% to about 70%; more preferably, from about 40% to about 65%) by weight of the total solution or (ii) a mixture of (1) a pharmaceutically acceptable long chain fatty acid in the amount of from about 20% to about 98% (preferably, from about 30% to about 70%; more preferably, from about 40% to about 65%) by weight of the total solution and (2) a pharmaceutically acceptable alcohol in the amount of from about 0% to about 15% (preferably, from about 6% to about 12%) by weight of the total solution and (c) a pharmaceutically acceptable surfactant in the amount of from about 0% to about 20% (preferably, from about 5% to about 10%) by weight of the total solution. In a more preferred embodiment of the invention, the solution is encapsulated in a soft elastic gelatin capsule (SEC) or a hard gelatin capsule.

An even more preferred composition of the invention is a solution comprising (a) a mixture of ritonavir in the amount of from about 1% to about 30% (preferably, from about 5% to about 25%) by weight of the total solution and another HIV protease inhibitor in the amount of from about 1% to about 50% (preferably, from about 5% to about 40%) by weight of the total solution, (b) a pharmaceutically acceptable organic solvent which comprises (i) oleic acid in the amount of from about 10% to about 98% (preferably, from about 30% to about 70%; more preferably, from about 40% to about 65%) by weight of the total solution or (ii) a mixture of (1) oleic acid in the amount or from about 10% to about 98% (preferably, from about 30% to about 70%; more preferably, from about 40% to about 65%) by weight of the total solution and (2) ethanol in the amount of from about 0% to about 12% (preferably, from about 10% to about 12%) by weight of the total solution or propylene glycol in the amount of from about 0% to about 10% (preferably, from about 5% to about 10%) by weight of the total solution or a mixture thereof in the amount of from about 0% to about 15% (preferably, from about 10% to about 15%) by weight of the total solution and (c) polyoxyl 35 castor oil in the amount of from about 0% to about 20% (preferably, from about 5% to about 10%) by weight of the total solution. In an even more preferred embodiment of the invention, the solution is encapsulated in a soft elastic gelatin capsule (SEC) or a hard gelatin capsule.

A most preferred composition of the invention is a solution comprising (a) a mixture of ritonavir in the amount of from about 1% to about 30% (preferably, from about 5% to about 25%) by weight of the total solution and (2S,3S,5S)-2-(2,6-dimethylphenoxyacetyl)amino-3-hydroxy-5-[2S-(1-tetrahydro-pyrimid-2-onyl)-3-methyl butanoyl]amino-1,6-diphenylhexane in the amount of from about 1% to about 50% (preferably, from about 5% to about 40%) by weight of the total solution, (b) a pharmaceutically acceptable organic solvent which comprises a mixture of (1) oleic acid in the amount of from about 10% to about 88% (preferably, from about 40% to about 65%) by weight of the total solution and (2) ethanol in the amount of about 10% by weight of the total solution and (c) polyoxyl 35 castor oil in the amount of about 10% by weight of the total solution. In a most preferred embodiment of the invention, the solution is encapsulated in a soft elastic gelatin capsule (SEC) or a hard gelatin capsule and the solution also comprises an antioxidant (preferably, BHT (butylated hydroxytoluene)) in the amount of from about 0.01% to about 0.08% by weight of the total solution (preferably, from about 0.01% to about 0.05% by weight of the total solution).

Another most preferred composition of the invention is a solution comprising (a) a mixture of ritonavir in the amount of from about 1% to about 30% (preferably, from about 5% to about 25%) by weight of the total solution and (2S,3S,5S)-2-(2,6-dimethylphenoxyacetyl)amino-3-hydroxy-5-[2S-(1-tetrahydro-pyrimid-2-onyl)-3-methyl butanoyl]amino-1,6-diphenylhexane in the amount of from about 1% to about 50% (preferably, from about 5% to about 40%) by weight of the total solution, (b) a pharmaceutically acceptable organic solvent which comprises a mixture of (1) oleic acid in the amount of from about 10% to about 88% (preferably, from about 40% to about 65%) by weight of the total solution and (2) propylene glycol in the amount of from about 5% to about 10% (preferably, from about 6% to about 8%) by weight of the total solution and (c) polyoxyl 35 castor oil in the amount of about 10% by weight of the total solution. In a most preferred embodiment of the invention, the solution is encapsulated in a soft elastic gelatin capsule (SEC) or a hard gelatin capsule and the solution also comprises an antioxidant (preferably, BHT (butylated hydroxytoluene)) in the amount of from about 0.01% to about 0.08% by weight of the total solution (preferably, from about 0.01% to about 0 05% by weight of the total solution).

A most highly preferred composition of the invention is a solution comprising (a) a mixture of ritonavir in the amount of about 5% by weight of the total solution and (2S,3S,5S)-2-(2,6-dimethylphenoxyacetyl)amino-3-hydroxy-5-[2S-(1-tetrahydro-pyrimid-2-onyl)-3-methyl butanoyl]amino-1,6-diphenylhexane in the amount of about 30% by weight of the total solution, (b) a pharmaceutically acceptable organic solvent which comprises a mixture of (1) oleic acid in the amount of about 45% by weight of the total solution and (2) ethanol in the amount of about 10% by weight of the total solution and (c) polyoxyl 35 castor oil in the amount of about 10% by weight of the total solution. In a most preferred embodiment of the invention, the solution is encapsulated in a soft elastic gelatin capsule (SEC) or a hard gelatin capsule and the solution also comprises an antioxidant (preferably, BHT (butylated hydroxytoluene)) in the amount of from about 0.01% to about 0.08% by weight of the total solution (preferably, from about 0.03% to about 0.05% by weight of the total solution).

Another most highly preferred composition of the invention is a solution comprising (a) a mixture of ritonavir in the amount of about 15% by weight of the total solution and (2S,3S,5S)-2-(2,6-dimethylphenoxyacetyl)amino-3-hydroxy-5-[2S-(1-tetrahydro-pyrimid-2-onyl)-3-methyl butanoyl]amino 1,6-diphenylhexane in the amount of about 15% by weight of the total solution, (b) a pharmaceutically acceptable organic solvent which comprises a mixture of (1) oleic acid in the amount of about 50% by weight of the total solution and (2) ethanol in the amount of about 10% by weight of the total solution and (c) polyoxyl 35 castor oil in the amount of about 10% by weight of the total solution. In a most preferred embodiment of the invention, the solution is encapsulated in a soft elastic gelatin capsule (SEC) or a hard gelatin capsule and the solution also comprises an antioxidant (preferably, BHT (butylated hydroxytoluene)) in the amount of from about 0.01% to about 0.08% by weight of the total solution (preferably, from about 0.03% to about 0.05% by weight of the total solution).

Another most highly preferred composition of the invention is a solution comprising (a) a mixture of ritonavir in the amount of about 15% by weight of the total solution and (2S,3S,5S)-2-(2,6-dimethylphenoxyacetyl) amino-3-hydroxy-5-[2S-(1-tetrahydro-pyrimid-2-onyl)-3-methyl butanoyl]amino-1,6-diphenylhexane in the amount of about 5% by weight of the total solution, (b) a pharmaceutically acceptable organic solvent which comprises a mixture of (1) oleic acid in the amount of about 60% by weight of the total solution and (2) ethanol in the amount of about 10% by weight of the total solution and (c) polyoxyl 35 castor oil in the amount of about 10% by weight of the total solution. In a most preferred embodiment of the invention, the solution is encapsulated in a soft elastic gelatin capsule (SEC) or a hard gelatin capsule and the solution also comprises an antioxidant (preferably, BHT (butylated hydroxytoluene)) in the amount of from about 0.01% to about 0.08% by weight of the total solution (preferably, from about 0.03% to about 0.05% by weight of the total solution).

Another most highly preferred composition of the invention is a solution comprising (a) a mixture of ritonavir in the amount of about 10% by weight of the total solution and (2S,3S,5S)-2-(2,6-dimethylphenoxyacetyl)amino-3-hydroxy-5-[2S-(1-tetrahydro-pyrimid-2-onyl)-3-methyl butanoyl]amino-1,6-diphenylhexane in the amount of about 20% by weight of the total solution, (b) a pharmaceutically acceptable organic solvent which comprises a mixture of (1) oleic acid in the amount of about 50% by weight of the total solution and (2) ethanol in the amount of about 10% by weight of the total solution and (c) polyoxyl 35 castor oil in the amount of about 10% by weight of the total solution. In a most preferred embodiment of the invention, the solution is encapsulated in a soft elastic gelatin capsule (SEC) or a hard gelatin capsule and the solution also comprises an antioxidant (preferably, BHT (butylated hydroxytoluene)) in the amount of from about 0.01% to about 0.08% by weight of the total solution (preferably, from about 0.03% to about 0.05% by weight of the total solution).

Another most highly preferred composition of the invention is a solution comprising (a) a mixture of ritonavir in the amount of about 13% by weight of the total solution and (2S,3S,5S)-2-(2,6-dimethylphenoxyacetyl)amino-3-hydroxy-5-[2S-(1-tetrahydro-pyrimid-2-onyl)-3-methyl butanoyl]amino-1,6-diphenylhexane in the amount of about 17% by weight of the total solution, (b) a pharmaceutically acceptable organic solvent which comprises a mixture of (1) oleic acid in the amount of about 50% by weight of the total solution and (2) ethanol in the amount of about 10% by weight of the total solution and (c) polyoxyl 35 castor oil in the amount of about 10% by weight of the total solution. In a most preferred embodiment of the invention, the solution is encapsulated in a soft elastic gelatin capsule (SEC) or a hard gelatin capsule and the solution also comprises an antioxidant (preferably, BHT (butylated hydroxytoluene)) in the amount of from about 0.01% to about 0.08% by weight of the total solution (preferably, from about 0.03% to about 0.05% by weight of the total solution).

Another most highly preferred composition of the invention is a solution comprising (a) a mixture of ritonavir in the amount of about 6.0% by weight of the total solution and (2S,3S,5S)-2-(2,6-dimethylphenoxyacetyl)amino-3-hydroxy-5-[2S-(1-tetrahydro-pyrimid-2-onyl)-3-methyl butanoyl]amino-1,6-diphenylhexane in the amount of about 24% by weight of the total solution, (b) a pharmaceutically acceptable organic solvent which comprises a mixture of (1) oleic acid in the amount of about 52.5% by weight of the total solution and (2) propylene glycol in the amount of about 7.5% by weight of the total solution and (c) polyoxyl 35 castor oil in the amount of about 10% by weight of the total solution. In a most preferred embodiment of the invention, the solution is encapsulated in a soft elastic gelatin capsule (SEC) or a hard gelatin capsule and the solution also comprises an antioxidant (preferably, BHT (butylated hydroxytoluene)) in the amount of from about 0.01% to about 0.08% by weight of the total solution (preferably, from about 0.01% to about 0.05% by weight of the total solution).

Another most highly preferred composition of the invention comprises a solution of (a) a mixture of ritonavir in the amount of about 5% by weight of the total solution and (2S,3S,5S)-2-(2,6-dimethylphenoxyacetyl)amino-3-hydroxy-5-[2S-(1-tetrahydro-pyrimid-2-onyl)-3-methyl butanoyl]amino-1,6-diphenylhexane in the amount of about 25% by weight of the total solution and (b) polyoxyl 35 castor oil in the amount of about 10% by weight of the total solution, in a pharmaceutically acceptable organic solvent which comprises a mixture of (1) oleic acid in the amount of about 52.5% by weight of the total solution and (2) propylene glycol in the amount of about 7.5% by weight of the total solution. In a most preferred embodiment of the invention, the solution is encapsulated in a soft elastic gelatin capsule (SEC) or a hard gelatin capsule and the solution also comprises an antioxidant (preferably, BHT (butylated hydroxytoluene)) in the amount of from about 0.01% to about 0.08% by weight of the total solution (preferably, from about 0.01% to about 0.05% by weight of the total solution).

Another most highly preferred composition of the invention is a solution comprising (a) a mixture of ritonavir in the amount of about 8% by weight of the total solution and (2S,3S,5S)-2-(2,6-dimethylphenoxyacetyl)amino-3-hydroxy-5-[2S-(1-tetrahydro-pyrimid-2-onyl)-3-methyl butanoyl]amino-1,6-diphenylhexane in the amount of about 24% by weight of the total solution, (b) a pharmaceutically acceptable organic solvent which comprises a mixture of (1) oleic acid in the amount of about 50.5% by weight of the total solution and (2) propylene glycol in the amount of about 7.5% by weight of the total solution and (c) polyoxyl 35 castor oil in the amount of about 10% by weight of the total solution. In a most preferred embodiment of the invention, the solution is encapsulated in a soft elastic gelatin capsule (SEC) or a hard gelatin capsule and the solution also comprises an antioxidant (preferably, BHT (butylated hydroxytoluene)) in the amount of from about 0.01% to about 0.08% by weight of the total solution (preferably, from about 0.01% to about 0.05% by weight of the total solution).

Another most highly preferred composition of the invention is a solution comprising (a) a mixture of ritonavir in the amount of about 8.25% by weight of the total solution and (2S,3S,5S)-2-(2,6-dimethylphenoxyacetyl)amino-3-hydroxy-5-[2S-(1-tetrahydro-pyrimid-2-onyl)-3-methyl butanoyl]amino-1,6-diphenylhexane in the amount of about 22% by weight of the total solution, (b) a pharmaceutically acceptable organic solvent which comprises a mixture of (1) oleic acid in the amount of about 52.25% by weight of the total solution and (2) propylene glycol in the amount of about 7.5% by weight of the total solution and (c) polyoxyl 35 castor oil in the amount of about 10% by weight of the total solution. In a most preferred embodiment of the invention, the solution is encapsulated in a soft elastic gelatin capsule (SEC) or a hard gelatin capsule and the solution also comprises an antioxidant (preferably, BHT (butylated hydroxytoluene)) in the amount of from about 0.01% to about 0.08% by weight of the total solution (preferably, from about 0.01% to about 0.05% by weight of the total solution).

Another most highly preferred composition of the invention is a solution comprising (a) a mixture of ritonavir in the amount of about 5% by weight of the total solution and (2S,3S,5S)-2-(2,6-dimethylphenoxyacetyl)amino-3-hydroxy-5-[2S-(1-tetrahydro-pyrimid-2-onyl)-3-methyl butanoyl]amino-1,6-diphenylhexane in the amount of about 30% by weight of the total solution, (b) a pharmaceutically acceptable organic solvent which comprises a mixture of (1) oleic acid in the amount of about 47.5% by weight of the total solution and (2) propylene glycol in the amount of about 7.5% by weight of the total solution and (c) polyoxyl 35 castor oil in the amount of about 10% by weight of the total solution. In a most preferred embodiment of the invention, the solution is encapsulated in a soft elastic gelatin capsule (SEC) or a hard gelatin capsule and the solution also comprises an antioxidant (preferably, BHT (butylated hydroxytoluene)) in the amount of from about 0.01% to about 0.08% by weight of the total solution (preferably, from about 0.01% to about 0.05% by weight of the total solution).

Another most highly preferred composition of the invention is a solution comprising (a) a mixture of ritonavir in the amount of about 13% by weight of the total solution and (2S,3S,5S)-2-(2,6-dimethylphenoxyacetyl)amino-3-hydroxy-5-[2S-(1-tetrahydro-pyrimid-2-onyl)-3-methyl butanoyl]amino 1,6-diphenylhexane in the amount of about 17% by weight of the total solution, (b) a pharmaceutically acceptable organic solvent which comprises a mixture of (1) oleic acid in the amount of about 52.5% by weight of the total solution and (2) propylene glycol in the amount of about 7.5% by weight of the total solution and (c) polyoxyl 35 castor oil in the amount of about 10% by weight of the total solution. In a most preferred embodiment of the invention, the solution is encapsulated in a soft elastic gelatin capsule (SEC) or a hard gelatin capsule and the solution also comprises an antioxidant (preferably, BHT (butylated hydroxytoluene)) in the amount of from about 0.01% to about 0.08% by weight of the total solution (preferably, from about 0.01% to about 0.05% by weight of the total solution).

Another most highly preferred composition of the invention is a solution comprising (a) a mixture of ritonavir in the amount of about 15% by weight of the total solution and (2S,3S,5S)-2-(2,6-dimethylphenoxyacetyl)amino-3-hydroxy-5-[2S-(1-tetrahydro-pyrimid-2-onyl)-3-methyl butanoyl]amino-1,6-diphenylhexane in the amount of about 15% by weight of the total solution, (b) a pharmaceutically acceptable organic solvent which comprises a mixture of (1) oleic acid in the amount of about 52.5% by weight of the total solution and (2) propylene glycol in the amount of about 7.5% by weight of the total solution and (c) polyoxyl 35 castor oil in the amount of about 10% by weight of the total solution. In a most preferred embodiment of the invention, the solution is encapsulated in a soft elastic gelatin capsule (SEC) or a hard gelatin capsule and the solution also comprises an antioxidant (preferably, BHT (butylated hydroxytoluene)) in the amount of from about 0.01% to about 0.08% by weight of the total solution (preferably, from about 0.01% to about 0 05% by weight of the total solution).

Another most highly preferred composition of the invention is a solution comprising (a) a mixture of ritonavir in the amount of about 10% by weight of the total solution and (2S,3S,5S)-2-(2,6-dimethylphenoxyacetyl)amino-3-hydroxy-5-[2S-(1-tetrahydro-pyrimid-2-onyl)-3-methyl butanoyl]amino-1,6-diphenylhexane in the amount of about 20% by weight of the total solution, (b) a pharmaceutically acceptable organic solvent which comprises a mixture of (1) oleic acid in the amount of about 52.5% by weight of the total solution and (2) propylene glycol in the amount of about 7.5% by weight of the total solution and (c) polyoxyl 35 castor oil in the amount of about 10% by weight of the total solution. In a most preferred embodiment of the invention, the solution is encapsulated in a soft elastic gelatin capsule (SEC) or a hard gelatin capsule and the solution also comprises an antioxidant (preferably, BHT (butylated hydroxytoluene)) in the amount of from about 0.01% to about 0.08% by weight of the total solution (preferably, from about 0.01% to about 0.05% by weight of the total solution).

In the compositions of the invention, preferred HIV protease inhibitors are selected from ritonavir, (2S,3S,5S)-2-(2,6-dimethylphenoxyacetyl)amino-3-hydroxy-5-[2S-(1-tetrahydro-pyrimid-2-onyl)-3-methyl butanoyl]amino-1,6-diphenylhexane, indinavir, saquinavir, nelfinavir and VX-478.

In the compositions of the invention, preferred combinations of HIV protease inhibitors include ritonavir and (2S, 3S,5S)-2-(2,6-dimethylphenoxyacetyl)amino-3-hydroxy-5-[2S-(1-tetrahydro-pyrimid-2-onyl)-3-methyl butanoyl] amino-1,6-diphenylhexane, ritonavir and indinavir, ritonavir and saquinavir, ritonavir and nelfinavir, ritonavir and VX-478, saquinavir and nelfinavir, indinavir and nelfinavir, nelfinavir and (2S,3S,5S)-2-(2,6-dimethylphenoxyacetyl) amino-3-hydroxy-5-[2S-(1-tetrahydro-pyrimid-2-onyl)-3-methyl butanoyl]amino-1,6-diphenylhexane and nelfinavir arid VX-478.

In the compositions of the invention which comprise a mixture of ritonavir and (2S,3S,5S)-2-(2,6-dimethylphenoxyacetyl)amino-3-hydroxy-5-[2S-(1-tetrahydro-pyrimid-2-onyl)-3-methyl butanoyl]amino-1,6-diphenylhexane, the ratio (w/w) of ritonavir to (2S,3S,5S)-2-(2,6-dimethylphenoxyacetyl)amino-3-hydroxy-5-[2S-(1-tetrahydro-pyrimid-2-onyl)-3-methyl butanoyl]amino-1,6-diphenylhexane ranges from about 1:16 to about 5:1 (preferably, from about 1:8 to about 3:1).

The compounds of formula I, II and IV contain two or more asymmetric carbon atoms and thus can exist as pure diastereomers, mixtures of diastereomers, diastereomeric racemates or mixtures of diastereomeric racemates. The present invention is intended to include within its scope all of the isomeric forms. The terms "R" and "S" configuration as used herein are as defined by IUPAC 1974 Recommendations for Section E, Fundamental Stereochemistry, Pure Appl. Chem. (1976) 45, 13–30.

The preferred isomer of the compound of formula II is; (2S,3S,5S)-5-(N-(N-((N-Methyl-N-((2-isopropyl-4-thiazolyl)methyl)-amino)carbonyl)-valinyl)amino)-2-(N-((5-thiazolyl)methoxycarbonyl)amino)-1,6-diphenyl-3-hydroxyhexane (compound III). The preferred isomer of the compound of formula IV is (2S,3S,5S)-2-(2,6-dimethylphenoxyacetyl)amino-3-hydroxy-5-[2S-(1-tetrahydro-pyrimid-2-onyl)-3-methyl butanoyl]amino-1,6-diphenylhexane (compound V).

The term "lower alkyl" as used herein refers to straight or branched chain alkyl radicals containing from 1 to 6 carbon atoms including, but not limited to, methyl, ethyl, n-propyl, iso-propyl, n-butyl, iso-butyl, sec-butyl, n-pentyl, 1-methylbutyl, 2,2-dimethylbutyl, 2-methylpentyl, 2,2-dimethylpropyl, n-hexyl and the like.

The HIV protease inhibiting compounds can be used in the form of salts derived from inorganic or organic acids.

These salts include but are not limited to the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxyethanesulfonate (isethionate), lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, p-toluenesulfonate and undecanoate. Also, the basic nitrogen-containing groups can be quaternized with such agents as loweralkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids which may be employed to form pharmaceutically acceptable acid addition salts include such inorganic acids as hydrochloric acid, sulphuric acid and phosphoric acid and such organic acids as oxalic acid, maleic acid, succinic acid and citric acid. Other salts include salts with alkali metals or alkaline earth metals, such as sodium, potassium, calcium or magnesium or with organic bases.

The composition and preparation of the soft elastic gelatin capsule itself is well known in the art. The composition of a soft elastic gelatin capsule typically comprises from about 30% to about 50% by weight of gelatin NF, from about 10% to about 40% by weight of a plasticizer or a blend of plasticizers and from about 25% to about 40% by weight of water. Plasticizers useful in the preparation of soft elastic gelatin capsules are glycerin, sorbitol or sorbitol derivatives (for example, sorbitol-special and the like) or propylene glycol and the like; or combinations thereof.

The soft elastic gelatin capsule material can also comprise additives such as preservatives, opacifiers, pigments, dyes or flavors and the like.

Various methods can be used for manufacturing and filling the soft elastic gelatin capsules, for example, a seamless capsule method, a rotary method (developed by Scherer) or a method using a Liner machine or an Accogel machine and the like. Also various manufacturing machines can be used for manufacturing the capsules.

Typically, the soft elastic gelatin capsule is prepared by (1) preparing the gel mass, (2) encapsulating the fill material (forming, filling and sealing the capsule) and (3) softgel drying.

During gel mass preparation, the ingredients comprising the gel mass (typically, gelatin, water and plasticizer) are mixed to form a uniform fluff. After blending, the fluff gel mass is melted, preferably, under vacuum, and the melted gel mass is transferred to heated receivers. Colorants or other additives can be added to the melted gel mass, which is then blended until uniform.

In one method a rotary die encapsulation apparatus is then used to encapsulate the liquid capsule fill. In general, in this method two gel ribbons are fed between two rotating dies. The dies contain paired pockets which form the shape of the softgel and provide the sealing mechanism. At the moment the two die half pockets line up, the fill material is injected through an encapsulation wedge in between the gel ribbons. The softgel is formed and sealed as a result of pressure between the dies and heat applied by the encapsulation wedge.

Finally, the filled softgels are dried. In one method the filled softgels are first placed in a rotary drier in a low humidity, forced air environment. A final step in the drying process involves discharging the filled softgels from the rotary drier and placing them in a monolayer on shallow drying trays, over which is circulated low humidity air of less than 50% relative humidity. The drying process is stopped by transferring the softgels into deep holding trays.

Preferred soft elastic gelatin capsules are manufactured by R. P. Scherer Corp.

Hard gelatin capsules can be purchased from Capsugel, Greenwood, S.C. and other suppliers. Capsules are filled manually or by capsule filling machine. The target filling volume/weight depends on the potency of the filling solution in combination with the desired dosage strength.

In general, the compositions of this invention can be prepared in the following manner. The pharmaceutically acceptable long chain fatty acid and the pharmaceutically acceptable alcohol are mixed at room temperature, along with the antioxidant. The HIV protease inhibitor, or mixture of HIV protease inhibitors, is added and stirred until dissolved. The pharmaceutically acceptable surfactant is added with mixing. The appropriate volume of the resulting mixture needed to provide the desired dose of the HIV protease inhibiting compound(s) is filled into hard gelatin capsules or soft elastic gelatin capsules.

The following examples will serve to further illustrate the invention.

EXAMPLE 1
Non-Formulated Capsule

An amount of compound III (free base) equivalent to a 5 mg/kg dose was placed in hard gelatin capsules (gray, size 0). These capsules were administered to fasted dogs with 10 ml of water.

EXAMPLE 2
Capsule

An amount of compound III (free base) equivalent to a 5 mg/kg dose was placed in hard gelatin capsules (gray, size 0). These capsules were administered to non-fasted dogs with ten milliliter of water.

EXAMPLE 3
Capsule

An amount of the bis-tosylate salt of compound III equivalent to a 5 mg/kg dose of compound III (base equivalent) was filled into hard gelatin capsules (gray, size 0). These capsules were administered to fed dogs with ten milliliter of water.

EXAMPLE 4
Capsule

| Component | % By Weight |
| --- | --- |
| ritonavir (free base) | 20 |
| Ethanol (USP, 200 proof) | 10 |
| Oleic acid, 6321, NF | 69.99 |
| Butylated hydroxy toluene (BHT), NF | 0.01 |

EXAMPLE 5
Capsule

| Component | % By Weight |
| --- | --- |
| ritonavir (free base) | 20 |
| Ethanol (USP, 200 proof) | 10 |
| Tween ® 80 (NF) | 5 |
| Oleic acid, 6321, NF | 64.99 |
| Butylated hydroxy toluene (BHT), NF | 0.01 |

EXAMPLE 6
Capsule

| Component | % By Weight |
| --- | --- |
| ritonavir (free base) | 20 |
| Ethanol (USP, 200 proof) | 10 |
| Tween ® 20 (NF) | 5 |
| Oleic acid, 6321, NF | 64.99 |
| Butylated hydroxy toluene (BHT), NF | 0.01 |

EXAMPLE 7
Capsule or SEC

| Component | % By Weight |
| --- | --- |
| ritonavir (free base) | 20 |
| Ethanol (USP, 200 proof) | 10 |
| polyoxyl 35 castor oil (Cremophor ® EL) | 5 |
| Oleic acid, 6321, NF | 64.99 |
| Butylated hydroxy toluene (BHT), NF | 0.01 |

The mixing tank was purged with nitrogen. Oleic acid (649.9 g) and ethanol (100 g) were mixed in the tank. This solution was warmed to about 33° C. (28–37° C.) and maintained at that temperature. The butylated hydroxytoluene (0.1 g) was charged into the tank and mixed until the solution was clear. The ritonavir (200 g) was slowly charged into the tank and mixed until the solution was clear. The polyoxyl 35 castor oil (50 g) was added to the tank and mixed. Heating was discontinued and the solution allowed to cool to amibient temperature (20–30° C.). The resulting solution was filled into soft elastic capsules (0.5 g of solution/SEC) to provide a dosage of 100 mg of ritonavir/SEC or 1.0 g of solution/SEC to provide a dosage of 200 mg of ritonavir/SEC.

EXAMPLE 8
Capsule

| Component | % By Weight |
| --- | --- |
| ritonavir (free base) | 20 |
| Ethanol (USP, 200 proof) | 10 |
| polyoxyl 35 castor oil (Cremophor ® EL) | 4.5 |
| Sorbitan monooleate | 0.5 |

| Component | % By Weight |
|---|---|
| Oleic acid, 6321, NF | 64.99 |
| Butylated hydroxy toluene (BHT), NF | 0.01 |

EXAMPLE 9

Capsule or SEC

| Component | % By Weight |
|---|---|
| ritonavir (free base) | 20 |
| Ethanol (USP, 200 proof) | 10 |
| polyoxyl 35 castor oil (Cremophor ® EL) | 10 |
| Oleic acid, 6321, NF | 59.99 |
| Butylated hydroxy toluene (BHT), NF | 0.01 |

The mixing tank was purged with nitrogen. Oleic acid (599.9 g) and ethanol (100 g) were mixed in the tank. This solution was warmed to about 33° C. (28–37° C.) and maintained at that temperature. The butylated hydroxytoluene (0.1 g) was charged into the tank and mixed until the solution was clear. The ritonavir (200 g) was slowly charged into the tank and mixed until the solution was clear. The polyoxyl 35 castor oil (100 g) was added to the tank and mixed. Heating was discontinued and the solution allowed to cool to amibient temperature (20–30° C.). The resulting solution was filled into soft elastic capsules (0.5 g of solution/SEC) to provide a dosage of 100 mg of ritonavir/SEC or 1.0 g of solution/SEC to provide a dosage of 200 mg of ritonavir/SEC.

EXAMPLE 10

SEC

| Component | % By Weight |
|---|---|
| ritonavir (free base) | 20 |
| Ethanol (USP, 200 proof) | 12 |
| polyoxyl 35 castor oil (Cremophor ® EL) | 6 |
| Oleic acid, 6321, NF | 61.95 |
| Butylated hydroxy toluene (BHT), NF | 0.05 |

The mixing tank was purged with nitrogen. Ethanol (118 g) was weighed out and blanketed with nitrogen. Ethanol (2 g) and butylated hydroxytoluene (0.5 g) were charged into a second mixing tank and mixed until uniform under a blanket of nitrogen. The main mixing tank was set for a temperature of 28° C. (range 23–33° C.). Oleic acid (614.5 g) was charged into the main mixing tank and mixing began. Ritonavir (200 g) was charged into the main mixing tank while mixing and mixed until uniform. The ethanol and and ethanol/butylated hydroxytoluene mixture were charged into the main mixing tank and mixed until clear. The polyoxyl 35 castor oil (60 g) was charged into the main mixing tank. Oleic acid (5 g) was charged into the main mixing tank and mixed until clear. The resulting solution was discharged through a 70 mesh or finer filter for storage at 2–8° C. under nitrogen prior to encapsulation. The resulting solution was filled into soft elastic capsules (1000 mg of solution/SEC) to provide a dosage of 200 mg of ritonavir/SEC or (500 mg of solution/SEC) to provide a dosage of 100 mg of ritonavir/SEC.

EXAMPLE 11

SEC

| Component | % By Weight |
|---|---|
| compound V (free base) | 30 |
| Ethanol (USP, 200 proof) | 10 |
| polyoxyl 35 castor oil (Cremophor ® EL) | 10 |
| Oleic acid, 6321, NF | 49.99 |
| Butylated hydroxy toluene (BHT), NF | 0.01 |

The mixing tank was purged with nitrogen. Oleic acid (499.9 g) and ethanol (100 g) were mixed in the tank. The butylated hydroxytoluene (0.1 g) was charged into the tank and mixed until the solution was clear. The Compound V (300 g) was slowly charged into the tank and mixed until the solution was clear. The polyoxyl 35 castor oil (100 g) was added to the tank and mixed. The resulting solution was filled into soft elastic capsules (0.333 g of solution/SEC) to provide a dosage of 100 mg of compound V/SEC or 0.667 g of solution/SEC to provide a dosage of 200 mg of compound V/SEC.

EXAMPLE 12

Capsule

| Component | % By Weight |
|---|---|
| ritonavir (free base) | 9 |
| compound V (free base) | 27 |
| Ethanol (USP, 200 proof) | 10 |
| polyoxyl 35 castor oil (Cremophor ® EL) | 10 |
| Oleic acid, 6321, NF | 43.99 |
| Butylated hydroxy toluene (BHT), NF | 0.01 |

Example 13

Capsule

| Component | % By Weight |
|---|---|
| ritonavir (free base) | 7.5 |
| compound V (free base) | 30 |
| Ethanol (USP, 200 proof) | 10 |
| polyoxyl 35 castor oil (Cremophor ® EL) | 10 |
| Oleic acid, 6321, NF | 42.49 |
| Butylated hydroxy toluene (BHT), NF | 0.01 |

EXAMPLE 14

Capsule

| Component | % By Weight |
|---|---|
| ritonavir (free base) | 17.5 |
| compound V (free base) | 17.5 |
| Ethanol (USP, 200 proof) | 10 |
| polyoxyl 35 castor oil (Cremophor ® EL) | 10 |

-continued

| Component | % By Weight |
|---|---|
| Oleic acid, 6321, NF | 44.99 |
| Butylated hydroxy toluene (BHT), NF | 0.01 |

EXAMPLE 15

Capsule

| Component | % By Weight |
|---|---|
| ritonavir (free base) | 14 |
| compound V (free base) | 28 |
| Ethanol (USP, 200 proof) | 10 |
| polyoxyl 35 castor oil (Cremophor ® EL) | 10 |
| Oleic acid, 6321, NF | 37.99 |
| Butylated hydroxy toluene (BHT), NF | 0.01 |

EXAMPLE 16

Capsule

| Component | % By Weight |
|---|---|
| ritonavir (free base) | 9 |
| compound V (free base) | 27 |
| Ethanol (USP, 200 proof) | 5 |
| polyoxyl 35 castor oil (Cremophor ® EL) | 10 |
| Oleic acid, 6321, NF | 48.99 |
| Butylated hydroxy toluene (BHT), NF | 0.01 |

EXAMPLE 17

Capsule

| Component | % By Weight |
|---|---|
| ritonavir (free base) | 7.5 |
| compound V (free base) | 30 |
| Ethanol (USP, 200 proof) | 5 |
| polyoxyl 35 castor oil (Cremophor ® EL) | 10 |
| Oleic acid, 6321, NF | 47.49 |
| Butylated hydroxy toluene (BHT), NF | 0.01 |

EXAMPLE 18

SEC

| Component | % By Weight |
|---|---|
| ritonavir (free base) | 5 |
| compound V (free base) | 30 |
| Ethanol (USP, 200 proof) | 10 |
| polyoxyl 35 castor oil (Cremophor ® EL) | 10 |
| Oleic acid, 6321, NF | 44.99 |
| Butylated hydroxy toluene (BHT), NF | 0.01 |

The mixing tank was purged with nitrogen. Oleic acid (449.9 g) and ethanol (100 g) were mixed in the tank. The butylated hydroxytoluene (0.1 g) was charged into the tank and mixed until the solution was clear. The ritonavir (50 g) was slowly charged into the tank and mixed until the solution was clear. The Compound V (300 g) was slowly charged into the tank and mixed until the solution was clear. The polyoxyl 35 castor oil (100 g) was added to the tank and mixed. The resulting solution was stored at 2–8° C. before being filled into soft elastic capsules.

EXAMPLE 19A

SEC

| Component | % By Weight |
|---|---|
| ritonavir (free base) | 15 |
| compound V (free base) | 15 |
| Ethanol (USP, 200 proof) | 10 |
| polyoxyl 35 castor oil (Cremophor ® EL) | 10 |
| Oleic acid, 6321, NF | 49.99 |
| Butylated hydroxy toluene (BHT), NF | 0.01 |

The mixing tank was purged with nitrogen. Oleic acid (499.9 g) and ethanol (100 g) were mixed in the tank. The butylated hydroxytoluene (0.1 g) was charged into the tank and mixed until the solution was clear. The ritonavir (150 g) was slowly charged into the tank and mixed until the solution was clear. Compound V (150 g) was slowly charged into the tank and mixed until the solution was clear. The polyoxyl 35 castor oil (100 g) was added to the tank and mixed. The resulting solution was filled into soft elastic capsules (1.0 g of solution/SEC) to provide a dosage of 150 mg each of ritonavir and compound V/SEC.

EXAMPLE 19B

SEC

| Component | % By Weight |
|---|---|
| ritonavir (free base) | 15 |
| compound V (free base) | 15 |
| Ethanol (USP, 200 proof) | 10 |
| polyoxyl 35 castor oil (Cremophor ® EL) | 5 |
| Oleic acid, 6321, NF | 54.99 |
| Butylated hydroxy toluene (BHT), NF | 0.01 |

EXAMPLE 20

SEC

| Component | % By Weight |
|---|---|
| ritonavir (free base) | 15 |
| compound V (free base) | 5 |
| Ethanol (USP, 200 proof) | 10 |
| polyoxyl 35 castor oil (Cremophor ® EL) | 10 |
| Oleic acid, 6321, NF | 59.99 |
| Butylated hydroxy toluene (BHT), NF | 0.01 |

EXAMPLE 21

SEC

| Component | % By Weight |
|---|---|
| ritonavir (free base) | 10 |
| compound V (free base) | 20 |
| Propylene glycol (USP) | 7.5 |
| Oleic acid, 6321, NF | 52.47 |
| polyoxyl 35 castor oil (Cremophor ® EL) | 10 |
| Butylated hydroxy toluene (BHT), NF | 0.03 |

EXAMPLE 22

SEC

| Component | % By Weight |
|---|---|
| ritonavir (free base) | 10 |
| compound V (free base) | 20 |
| Propylene glycol (USP) | 6 |
| Oleic acid, 6321, NF | 53.97 |
| polyoxyl 35 castor oil (Cremophor ® EL) | 10 |
| Butylated hydroxy toluene (BHT), NF | 0.03 |

EXAMPLE 23

SEC

| Component | % By Weight |
|---|---|
| ritonavir (free base) | 11 |
| compound V (free base) | 22 |
| Propylene glycol (USP) | 7.5 |
| Oleic acid, 6321, NF | 49.47 |
| polyoxyl 35 castor oil (Cremophor ® EL) | 10 |
| Butylated hydroxy toluene (BHT), NF | 0.03 |

EXAMPLE 24

SEC

| Component | % By Weight |
|---|---|
| ritonavir (free base) | 9 |
| compound V (free base) | 27 |
| Propylene glycol (USP) | 7.5 |
| Oleic acid, 6321, NF | 46.47 |
| polyoxyl 35 castor oil (Cremophor ® EL) | 10 |
| Butylated hydroxy toluene (BHT), NF | 0.03 |

EXAMPLE 25

SEC

| Component | % By Weight |
|---|---|
| ritonavir (free base) | 6.5 |
| compound V (free base) | 32.5 |
| Propylene glycol (USP) | 7.5 |
| Oleic acid, 6321, NF | 43.47 |
| polyoxyl 35 castor oil (Cremophor ® EL) | 10 |
| Butylated hydroxy toluene (BHT), NF | 0.03 |

EXAMPLE 26

SEC

| Component | % By Weight |
|---|---|
| ritonavir (free base) | 4.4 |
| compound V (free base) | 35 |
| Propylene glycol (USP) | 7.5 |
| Oleic acid, 6321, NF | 53.07 |
| polyoxyl 35 castor oil (Cremophor ® EL) | 10 |
| Butylated hydroxy toluene (BHT), NF | 0.03 |

EXAMPLE 27

SEC

| Component | % By Weight |
|---|---|
| ritonavir (free base) | 5 |
| compound V (free base) | 30 |
| Propylene glycol (USP) | 7.5 |
| Oleic acid, 6321, NF | 47.47 |
| polyoxyl 35 castor oil (Cremophor ® EL) | 10 |
| Butylated hydroxy toluene (BHT), NF | 0.03 |

EXAMPLE 28

SEC

| Component | % By Weight |
|---|---|
| ritonavir (free base) | 5 |
| compound V (free base) | 30 |
| Propylene glycol (USP) | 6 |
| Oleic acid, 6321, NF | 48.97 |
| polyoxyl 35 castor oil (Cremophor ® EL) | 10 |
| Butylated hydroxy toluene (BHT), NF | 0.03 |

EXAMPLE 29

SEC

| Component | % By Weight |
|---|---|
| ritonavir (free base) | 10 |
| compound V (free base) | 20 |
| Propylene glycol (USP) | 7.5 |
| Oleic acid, 6321, NF | 52.47 |
| polyoxyl 35 castor oil (Cremophor ® EL) | 10 |
| Butylated hydroxy toluene (BHT), NF | 0.03 |

The mixing tank was purged with nitrogen. Oleic acid (524.7 g) and propylene glycol (75 g) were mixed in the tank. The butylated hydroxytoluene (0.3 g) was charged into the tank and mixed until the solution was clear. The ritonavir (100 g) was slowly charged into the tank and mixed until the solution was clear. Heat was applied as necessary. The polyoxyl 35 castor oil (100 g) was added to the tank and mixed. Compound V (200 g) was slowly charged into the tank and mixed until the solution was clear. Heat was applied as necessary. The resulting solution was stored at 2–8° C. before being filled into soft elastic capsules.

EXAMPLE 30

SEC

| Component | % By Weight |
|---|---|
| ritonavir (free base) | 5.5 |
| compound V (free base) | 33 |
| Propylene glycol (USP) | 7.5 |
| Oleic acid, 6321, NF | 43.97 |
| polyoxyl 35 castor oil (Cremophor ® EL) | 10 |
| Butylated hydroxy toluene (BHT), NF | 0.03 |

EXAMPLE 31

SEC

| Component | % By Weight |
|---|---|
| ritonavir (free base) | 6.0 |
| compound V (free base) | 24 |
| Propylene glycol (USP) | 7.5 |
| Oleic acid, 6321, NF | 52.47 |
| polyoxyl 35 castor oil (Cremophor ® EL) | 10 |
| Butylated hydroxy toluene (BHT), NF | 0.03 |

The mixing tank was purged with nitrogen. Oleic acid (524.7 g) and butylated hydroxytoluene (0.3 g) were charged into the tank and mixed. Propylene glycol (75.0 g) was charged into the tank. The ritonavir (60 g) was slowly charged into the tank and mixed until the solution was clear. Heat may be applied as necessary. The polyoxyl 35 castor oil (100 g) was added to the tank and mixed. Compound V (240 g) was slowly charged into the tank and mixed until the solution was clear. Heat may be applied as necessary. The resulting solution was filled into soft elastic capsules (1.0 g of solution/SEC) to provide a dosage of 60 mg of ritonavir and 240 mg of compound V/SEC.

EXAMPLE 32

SEC

| Component | % By Weight |
|---|---|
| ritonavir (free base) | 5 |
| compound V (free base) | 25 |
| Propylene glycol (USP) | 7.5 |
| Oleic acid, 6321, NF | 52.47 |
| polyoxyl 35 castor oil (Cremophor ® EL) | 10 |
| Butylated hydroxy toluene (BHT), NF | 0.03 |

EXAMPLE 33

SEC

| Component | % By Weight |
|---|---|
| ritonavir (free base) | 8 |
| compound V (free base) | 24 |
| Propylene glycol (USP) | 7.5 |
| Oleic acid, 6321, NF | 50.47 |
| polyoxyl 35 castor oil (Cremophor ® EL) | 10 |
| Butylated hydroxy toluene (BHT), NF | 0.03 |

EXAMPLE 34

SEC

| Component | % By Weight |
|---|---|
| ritonavir (free base) | 8.25 |
| compound V (free base) | 22 |
| Propylene glycol (USP) | 7.5 |
| Oleic acid, 6321, NF | 52.22 |
| polyoxyl 35 castor oil (Cremophor ® EL) | 10 |
| Butylated hydroxy toluene (BHT), NF | 0.03 |

EXAMPLE 35

SEC

| Component | % By Weight |
|---|---|
| ritonavir (free base) | 20 |
| Propylene glycol (USP) | 5 |
| Ethanol (USP, 200 proof) | 5 |
| Oleic acid, 6321, NF | 69.99 |
| Butylated hydroxy toluene (BHT), NF | 0.01 |

EXAMPLE 36

SEC

| Component | % By Weight |
|---|---|
| ritonavir (free base) | 10 |
| compound V (free base) | 20 |

-continued

| Component | % By Weight |
|---|---|
| Ethanol (USP, 200 proof) | 10 |
| polyoxyl 35 castor oil (Cremophor ® EL) | 10 |
| Oleic acid, 6321, NF | 49.99 |
| Butylated hydroxy toluene (BHT), NF | 0.01 |

The mixing tank was purged with nitrogen. Oleic acid (499.9 g) and ethanol (100 g) were mixed in the tank. The butylated hydroxytoluene (0.1 g) was charged into the tank and mixed until the solution was clear. The ritonavir (100 g) was slowly charged into the tank and mixed until the solution was clear. The Compound V (200 g) was slowly charged into the tank and mixed until the solution was clear. The polyoxyl 35 castor oil (100 g) was added to the tank and mixed. The resulting solution was stored at 2–8° C. before being filled into soft elastic capsules.

EXAMPLE 37

SEC

| Component | % By Weight |
|---|---|
| ritonavir (free base) | 13 |
| compound V (free base) | 17 |
| Ethanol (USP, 200 proof) | 10 |
| polyoxyl 35 castor oil (Cremophor ® EL) | 10 |
| Oleic acid, 6321, NF | 49.99 |
| Butylated hydroxy toluene (BHT), NF | 0.01 |

EXAMPLE 38

SEC

| Component | % By Weight |
|---|---|
| ritonavir (free base) | 13 |
| compound V (free base) | 17 |
| Propylene glycol (USP) | 7.5 |
| polyoxyl 35 castor oil (Cremophor ® EL) | 10 |
| Oleic acid, 6321, NF | 52.47 |
| Butylated hydroxy toluene (BHT), NF | 0.03 |

EXAMPLE 39

SEC

| Component | % By Weight |
|---|---|
| ritonavir (free base) | 15 |
| compound V (free base) | 15 |
| Propylene glycol (USP) | 7.5 |
| polyoxyl 35 castor oil (Cremophor ® EL) | 10 |
| Oleic acid, 6321, NF | 52.47 |
| Butylated hydroxy toluene (BHT), NF | 0.03 |

EXAMPLE 40

(2S,3S,5S)-5-(N-(N-((N-Methyl-N-((2-isopropyl-4-thiazolyl)methyl)-amino)amino)carbonyl)valinyl)amino)-2-(N-((5-thiazolyl)methoxycarbonyl)amino)-1,6-diphenyl-3-hydroxyhexane (ritonavir: compound III)

Compound III can be prepared according to the procedures disclosed in U.S. Pat. No. 5,541,206, issued Jul. 30, 1996 and U.S. Pat. No. 5,491,253, issued Feb. 13, 1996, U.S. Pat. No. 5,567,823, issued Oct. 22,1996, U.S. patent application Ser. No. 08/673,445, filed Jun. 28, 1996, U.S. patent Ser. application No. 08/673,445, filed Jun. 28, 1996 and U.S. patent application Ser. No. 08/862,951, filed May 30, 1997, all of which are incorporated herein by reference.

EXAMPLE 41

(2S,3S,5S)-2-(2,6-Dimethylphenoxyacetyl)amino-3-hydroxy-5-[2S-(1-tetrahydro-pyrimid-2-onyl)-3-methyl butanoyl]amino-1,6-diphenylhexane (compound V)

Compound V can be prepared according to the methods disclosed in U.S. patent application Ser. No. 08/753, filed Nov. 21, 1996 and International Patent Application No. WO97/21685, published Jun. 19,1997, and which are incorporated herein by reference.

PROTOCOL FOR ORAL BIOAVAILABILITY STUDIES

Dogs (beagle dogs, mixed sexes, weighing 7–14 kg) were fasted overnight prior to dosing, but were permitted water ad libitum. Each dog received a 100 $\mu$g/kg subcutaneous dose of histamine approximately 30 minutes prior to dosing. Each dog received a single solid dosage form corresponding to a 5 mg/kg dose of the drug. The dose was followed by approximately 10 milliliters of water. Blood samples were obtained from each animal prior to dosing and 0.25, 0.5, 1.0, 1.5, 2, 3, 4, 6, 8, 10 and 12 hours after drug administration. The plasma was separated from the red cells by centrifugation and frozen (–30° C.) until analysis. Concentrations of parent drug were determined by reverse phase HPLC with low wavelength UV detection following liquid-liquid extraction of the plasma samples. The parent drug area under the curve was calculated by the trapezoidal method over the time course of the study. The absolute bioavailability of each test composition was calculated by comparing the area under the curve after oral dosing to that obtained from a single intravenous dose. Each capsule or capsule composition was evaluated in a group containing at least six dogs; the values reported are averages for each group of dogs. The average bioavailability data for the compositions of the Examples is shown in Table I.

TABLE 1

| Example No. | Mean % Bioavailability |
|---|---|
| Example 1 | 0.0 |
| Example 2 | 0.0 |
| Example 3 | 2.5 |
| Example 4 | 39 |
| Example 5 | 38.8 |
| Example 6 | 39.6 |
| Example 7 | 55.7 |
| Example 8 | 40.3 |
| Example 9 | 61.9 |

This data indicates that solution compositions provided significantly better bioavailability than non-formulated compound III. Additionally, the solution composition, encapsulated in hard gelatin capsule or soft elastic capsule, demonstrated greatly improved bioavailability.

Compounds I, II, III, IV and V are inhibitors of HIV protease. They are useful for inhibiting an HIV infection and treating AIDS in humans. Total daily dose of compound I, II or III administered to a human in single or divided doses may be in amounts, for example, from 0.001 to 1000 mg/kc body weight daily but more usually 0.1 to 50 mg/kg body weight daily. Total daily dose of compound IV or V administered to a human in single or divided doses may be in amounts, for example, from 0.001 to 300 mg/kg body weight daily and more usually 0.1 to 20 mg/kg body weight daily. Dosage unit compositions may contain such amounts of submultiples thereof to make up the daily dose. It will be understood, however, that the specific dose level for any particular patient will depend upon a variety of factors including the age, body weight, general health, sex, diet, time of administration, rate of excretion, drugs administered in combination and the severity of the particular disease undergoing therapy.

The foregoing is merely illustrative of the invention and is not intended to limit the invention to the disclosed compounds, methods and compositions. Variations and changes which are obvious to one skilled in the art are intended to be within the scope and nature of the invention which are defined in the appended claims.

What is claimed is:

1. A pharmaceutical composition for oral administration which is a solution comprising:
    (a) an HIV protease inhibiting compound which is (2S, 3S,5S)-5-(N-(N-((N-Methyl-N-((2-isopropyl-4-thiazolyl)methyl)-amino)carbonyl)valinyl)amino)-2-(N-((5-thiazolyl)methoxycarbonyl)amino)-1,6-diphenyl-3-hydroxyhexane (ritonavir),
    (b) a pharmaceutically acceptable organic solvent which comprises a pharmaceutically acceptable long chain fatty acid or a mixture of a pharmaceutically acceptable long chain fatty acid selected from the group consisting of saturated, mono-unsaturated and di-unsaturated $C_{12}$ to $C_{18}$ carboxylic acids which are liquids at room temperature and a pharmaceutically acceptable alcohol, and, optionally,
    (c) a pharmaceutically acceptable surfactant.

2. The composition of claim 1 comprising:
    (a) an HIV protease inhibiting compound which is (2S, 3S,5S)-5-(N-(N-((N-Methyl-N-((2-isopropyl-4-thiazolyl)methyl)-amino)carbonyl)valinyl)amino)-2-(N-((5-thiazolyl)methoxycarbonyl)amino)-1,6-diphenyl-3-hydroxyhexane (ritonavir), in the amount of from about 1% to about 50% by weight of the total solution,
    (b) a pharmaceutically acceptable organic solvent which comprises (i) a pharmaceutically acceptable long chain fatty acid selected from the group consisting of saturated, mono-unsaturated and di-unsaturated $C_{12}$ to $C_{18}$ carboxylic acids which are liquids at room temperature in the amount of from about 20% to about 99% by weight of the total solution or (ii) a mixture of (1) a pharmaceutically acceptable long chain fatty acid selected from the group consisting of saturated, mono-unsaturated and di-unsaturated $C_{12}$ to $C_{18}$ carboxylic acids which are liquids at room temperature in the amount of from about 20% to about 99% by weight of the total solution and (2) a pharmaceutically acceptable alcohol in the amount of from about 0% to about 15% by weight of the total solution and
    (c) a pharmaceutically acceptable surfactant in the amount of from about 0% to about 40% by weight of the total solution.

3. The composition of claim 1 wherein the solution is encapsulated in a hard gelatin capsule or a soft elastic gelatin capsule.

4. The composition of claim 1 wherein the solvent comprises:
    (1) a pharmaceutically acceptable long chain fatty acid selected from the group consisting of saturated, mono-unsaturated and di-unsaturated $C_{12}$ to $C_{18}$ carboxylic acids which are liquids at room temperature in the amount of from about 40% to about 70% by weight of the total solution and (2) ethanol or propylene glycol in the amount of from about 1% to about 15% by weight of the total solution or a mixture of ethanol and propylene glycol in the amount of from about 1% to about 15% by weight of the total solution.

5. The composition of claim 1 wherein the solvent comprises:
    (1) a pharmaceutically acceptable long chain fatty acid selected from the group consisting of saturated, mono-unsaturated and di-unsaturated $C_{12}$ to $C_{18}$ carboxylic acids which are liquids at room temperature in the amount of from about 40% to about 70% by weight of the total solution and (2) ethanol in the amount of from about 10% to about 12% by weight of the total solution or propylene glycol in the amount of from about 5% to about 10% by weight of the total solution or a mixture of ethanol and propylene glycol in the amount of from about 5% to about 15% by weight of the total solution.

6. The composition of claim 1 wherein the solvent comprises (1) oleic acid in the amount of from about 40% to about 70% by weight of the total solution and (2) ethanol in the amount of from about 10% to about 12% by weight of the total solution or propylene glycol in the amount of from about 5% to about 10% by weight of the total solution or a mixture of ethanol and propylene glycol in the amount of from about 10% to about 15% by weight of the total solution.

7. The composition of claim 1 comprising:
    (a) ritonavir in the amount of from about 1% to about 30% by weight of the total solution,
    (b) a pharmaceutically acceptable organic solvent which comprises (i) a pharmaceutically acceptable long chain fatty acid selected from the group consisting of saturated, mono-unsaturated and di-unsaturated $C_{12}$ to $C_{18}$ carboxylic acids which are liquids at room temperature in the amount of from about 40% to about 99% by weight of the total solution or (ii) a mixture of (1) a pharmaceutically acceptable long chain fatty acid selected from the group consisting of saturated, mono-unsaturated and di-unsaturated $C_{12}$ to $C_{18}$ carboxylic acids which are liquids at room temperature in the amount of from about 40% to about 99% by weight of the total solution and (2) a pharmaceutically acceptable alcohol in the amount of from about 0% to about 15% by weight of the total solution and
    (c) a pharmaceutically acceptable surfactant in the amount of from about 0% to about 20% by weight of the total solution.

8. The composition of claim 7 wherein the solution is encapsulated in a soft elastic gelatin capsule (SEC).

9. The composition of claim 7 comprising:
    (a) ritonavir in the amount of from about 5% to about 25% by weight of the total solution,
    (b) a pharmaceutically acceptable organic solvent which comprises (i) a pharmaceutically acceptable long chain fatty acid selected from the group consisting of saturated, mono-unsaturated and di-unsaturated $C_{12}$ to $C_{18}$ carboxylic acids which are liquids at room temperature in the amount of from about 30% to about 70% by weight of the total solution or (ii) a mixture of (1) a pharmaceutically acceptable long chain fatty acid selected from the group consisting of saturated, mono-unsaturated and di-unsaturated $C_{12}$ to $C_{18}$ carboxylic acids which are liquids at room temperature in the amount of from about 30% to about 70% by weight of the total solution and (2) a pharmaceutically acceptable alcohol in the amount of from about 6% to about 12% by weight of the total solution and (c) a pharmaceutically acceptable surfactant in the amount of from about 5% to about 10% by weight of the total solution.

10. The composition of claim 9 wherein the solution is encapsulated in a soft elastic gelatin capsule (SEC).

11. The composition of claim 1 comprising (a) ritonavir in the amount of from about 1% to about 30% by weight of the total solution, (b) a pharmaceutically acceptable organic solvent which comprises (i) oleic acid in the amount of from about 15% to about 99% by weight of the total solution or (ii) a mixture of (1) oleic acid in the amount of from about 15% to about 99% by weight of the total solution and (2) ethanol in the amount of from about 0% to about 12% by weight of the total solution or propylene glycol in the amount of from about 0% to about 10% by weight of the total solution or a mixture thereof in the amount of from about 0% to about 15% by weight of the total solution and (c) polyoxyl 35 castor oil in the amount of from about 0% to about 20% by weight of the total solution.

12. The composition of claim 11 comprising (a) ritonavir in the amount of from about 5% to about 25% by weight of the total solution, (b) a pharmaceutically acceptable organic solvent which comprises (i) oleic acid in the amount of from about 30% to about 70% by weight of the total solution or (ii) a mixture of (1) oleic acid in the amount of from about 30% to about 70% by weight of the total solution and (2) ethanol in the amount of from about 10% to about 12% by weight of the total solution or propylene glycol in the amount of from about 5% to about 10% by weight of the total solution or a mixture thereof in the amount of from about 10% to about 15% by weight of the total solution and (c) polyoxyl 35 castor oil in the amount of from about 5% to about 10% by weight of the total solution.

13. The composition of claim 11 wherein the solution is encapsulated in a soft elastic gelatin capsule (SEC).

14. The composition of claim 11 comprising (a) ritonavir in the amount of about 20% by weight of the total solution, (b) a pharmaceutically acceptable organic solvent which comprises a mixture of (1) oleic acid in the amount of from about 62% to about 64% by weight of the total solution and (2) ethanol in the amount of from about 10% to about 12% by weight of the total solution and (c) polyoxyl 35 castor oil in the amount of about 6% by weight of the total solution.

15. The composition of claim 11 comprising (a) ritonavir in the amount of about 20% by weight of the total solution, (b) a pharmaceutically acceptable organic solvent which comprises a mixture of (1) oleic acid in the amount of about 65% by weight of the total solution and (2) ethanol in the amount of about 10% by weight of the total solution and (c) polyoxyl 35 castor oil in the amount of about 5% by weight of the total solution.

16. The composition of claim 11 comprising (a) ritonavir in the amount of about 20% by weight of the total solution, (b) a pharmaceutically acceptable organic solvent which comprises a mixture of (1) oleic acid in the amount of about 60% by weight of the total solution and (2) ethanol in the amount of about 10% by weight of the total solution and (c) polyoxyl 35 castor oil in the amount of about 10% by weight of the total solution.

* * * * *

UNITED STATES PATENT AND TRADEMARK OFFICE
CERTIFICATE OF CORRECTION

PATENT NO.   : 6,232,333 B1
DATED        : May 15, 2001
INVENTOR(S)  : John Lipari et al.

It is certified that error appears in the above-identified patent and that said Letters Patent is hereby corrected as shown below:

Title Page,
Item [75], Inventors, replace "Ghosh, Lindenhurst, Il(US): Rong Gao, Park City, Il (US); Dilip Kaul, Gurnee, Il (US)" with -- Ghosh, Lindenhurst, Il (US) --.

Column 2,
Line 26, replace "Application No. W093/2336, published Nov. 25, 1993," with -- Application No. W093/23368, published November 25, 1993, --.

Signed and Sealed this

Twenty-fifth Day of March, 2003

JAMES E. ROGAN
*Director of the United States Patent and Trademark Office*